United States Patent
Wang et al.

(10) Patent No.: US 8,141,427 B2
(45) Date of Patent: Mar. 27, 2012

(54) PIEZOELECTRIC AND PIEZORESISTIVE CANTILEVER SENSORS

(75) Inventors: Zhong L Wang, Marietta, GA (US); Changshi Lao, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 966 days.

(21) Appl. No.: 12/132,720

(22) Filed: Jun. 4, 2008

(65) Prior Publication Data

US 2009/0301196 A1     Dec. 10, 2009

(51) Int. Cl.
*G01H 1/00* (2006.01)
(52) U.S. Cl. ......................................................... 73/579
(58) Field of Classification Search .................... 73/570, 73/579, 581
See application file for complete search history.

(56) References Cited

U.S. PATENT DOCUMENTS

| | | | |
|---|---|---|---|
| 7,032,454 B2 * | 4/2006 | Amano | 73/704 |
| 7,181,977 B2 * | 2/2007 | Thompson et al. | 73/777 |
| 7,330,007 B2 * | 2/2008 | Sugiura et al. | 318/456 |
| 2002/0174715 A1 * | 11/2002 | Kim et al. | 73/105 |
| 2005/0112621 A1 * | 5/2005 | Kim et al. | 435/6 |

* cited by examiner

*Primary Examiner* — Max Noori
(74) *Attorney, Agent, or Firm* — Bryan W. Bockhop; Bockhop & Associates, LLC

(57) ABSTRACT

An apparatus for sensing a target substance includes a substrate, an elongated electroactive cantilever, a functional layer and an electrical sensor. The elongated electroactive cantilever includes a first surface and an opposite second surface. The elongated electroactive cantilever includes an electroactive member extending outwardly from the substrate. The functional layer is applied to the first surface and includes a material that reacts with the target substance so that when the functional layer is in the presence of the target substance, the functional layer will cause a change in an electrical property of the electroactive cantilever. The electrical sensor is coupled to the electroactive cantilever and is configured to sense the electrical property of the electroactive cantilever.

18 Claims, 1 Drawing Sheet

PIEZOELECTRIC AND PIEZORESISTIVE CANTILEVER SENSORS

STATEMENT OF GOVERNMENT INTEREST

This invention was made with support from the U.S. government under grant number GIT Proj. No. E18-T52, awarded by the National Science Foundation. The government may have certain rights in the invention.

BACKGROUND OF THE INVENTION

1. Field of the Invention

The present invention relates to sensor systems and, more specifically, to a nanoscale substance sensor.

2. Description of the Prior Art

Substance sensors are used in a wide variety of applications, including medical diagnostics, contraband detection, chemical process metrology, hazardous substance detection and any process where the detection or measurement of a substance is necessary. Many different bulk substance detection and measuring tests are well known to those of skill in the chemical and biomedical arts. Such tests usually involve reaction of the target substance with a test material to induce a change is a physical property of the test material. For example, litmus paper is a well known test material for detecting the presence of acids.

In some applications, the target substance is present in extremely low concentrations and is, therefore, hard to detect using conventional bulk chemical testing systems. For example, detecting contraband (e.g., explosives and illegal narcotics) can be difficult in real time using conventional chemical testing. Detection systems for these types of substances often fail to detect a substance when it is present below a certain concentration, even though a dangerous amount may be present.

Certain animals, such as dogs, can be trained to detect a target substance by smelling it in the air. However, animals often give false positive results and false negative results. They also sometimes cannot detect a target substance when it is masked by another substance. Also, the training and maintenance of such animals is quite costly.

Recently, functionalized cantilever sensors have been developed to detect target substances. Such sensors employ a cantilever that has been functionalized on one side with a material that reacts to a target substance. When the material is exposed to the target substance in sufficient quantity, the material will induce surface stress on the cantilever, thereby causing it to deform. The deformation may be detected in one of several manners, including using an optical displacement sensor. Such cantilevers typically have a width in the tens of micrometers. While micro-scale cantilevers can provide real time data, their micro-scale width limits their sensitivity.

Currently, most cantilever sensors are made with micro-electro-mechanical systems (MEMS) mask and etching processes. A typical size of the cantilever is approximately tens of micrometers in width. This relatively large size of MEMS cantilevers limits the sensitivity of these sensors because the ratio of functionalized area to displacement is limited. Reducing the size of the cantilever would improve sensitivity, but existing displacement sensing systems become increasingly imprecise as the cantilever size is reduced.

Therefore, there is a need for a sensor system that can detect extremely low concentrations of target substances in real time with a high level of precision.

SUMMARY OF THE INVENTION

The disadvantages of the prior art are overcome by the present invention which, in one aspect, is an apparatus for sensing a target substance that includes a substrate, an elongated electroactive cantilever, a functional layer and an electrical sensor. The elongated electroactive cantilever includes a first surface and an opposite second surface. The elongated electroactive cantilever includes an electroactive member extending outwardly from the substrate. The functional layer is applied to the first surface and includes a material that reacts with the target substance so that when the functional layer is in the presence of the target substance, the functional layer will cause a change in an electrical property of the electroactive cantilever. The electrical sensor is coupled to the electroactive cantilever and is configured to sense the electrical property of the electroactive cantilever.

In another aspect, the invention is a method of making a sensor for sensing a target substance, in which an elongated electroactive cantilever is created. A selected surface of the elongated electroactive cantilever is functionalized with a functional material that reacts with the target substance so that when the functional material is in the presence of the target substance, the functional material will cause a change in an electrical property of the electroactive cantilever. The electrical sensor is coupled to the electroactive cantilever and is configured to sense the change in the electrical property of the electroactive cantilever.

In yet another aspect, the invention is a method of sensing a presence of a target substance in an environment. An electroactive cantilever that has been functionalized with a material that causes a change in an electrical property of the electroactive cantilever when the material interacts with the target substance is exposed to the environment. The electrical property of the electroactive cantilever is sensed.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1A:
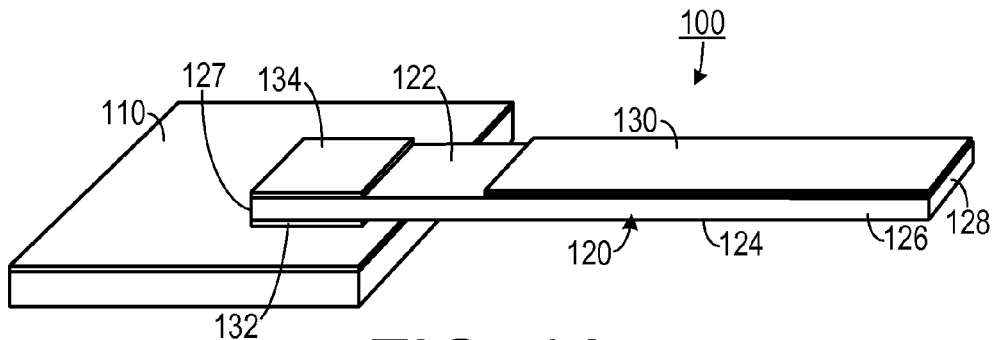
FIGS. 1A-1B are perspective views of a piezoelectric ribbon cantilever embodiment.

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." "Elongated piezoelectric structure" includes wires and ribbons, such as nanowires and nano-ribbons.

One representative embodiment of a target substance sensor includes a nano-scale electroactive cantilever that is functionalized with a material that reacts with the target substance. When the functionalized cantilever is exposed to an environment containing the target substance, molecules of the target substance will react with the functionalized layer (e.g., by being absorbed by the functionalized layer), thereby creating a surface energy differential between the functionalized side of the cantilever and the opposite side of the cantilever. This may result in bending of the cantilever, thereby changing an electrical property of the cantilever. This change in electrical properties of the cantilever may be measured, thereby detecting the presence of the target substance in the environment.

By using nanoscale cantilever structures (which employ, for example ZnO nano-ribbons or carbon nanotubes as electroactive members), in which displacement of the cantilevers may be readily detected using existing electrical detection devices, the devices disclosed herein exhibit extremely high sensitivity and selectivity. The large surface to volume ratio of ZnO nano-ribbons and carbon nanotubes greatly enhances the sensitivity of the cantilever sensors and the significant piezoelectricity of ZnO nano-ribbons and piezo-resistivity of carbon nanotubes provide a precise and stable signal for the detection system.

As shown in FIG. 1A, one embodiment of a sensor 100 for detecting a target substance includes a substrate 110 and an elongated electroactive cantilever 120 that includes a first surface 122 and an opposite second surface 124. The elongated electroactive cantilever 120 includes an electroactive member, such as a piezoelectric ZnO nanobelt 126 that extends outwardly from the substrate 110. (Other materials that could be used to make the electroactive member include wurtzite structured II-VI compounds, semiconductors and piezoelectric oxides.)

A functional layer 130 that includes a material that reacts with the target substance is applied to the first surface 122. The material of the functional layer 130 would be a material that reacts with or absorbs the target substance. (For example, a hydrophilic polymer could be used as the material if the target substance is water vapor.) When the functional layer 130 is in the presence of the target substance, the functional layer 130 causes a change in an electrical property of the electroactive cantilever 120. This change in electrical property can be a result of the functional layer 130 expanding as a result of molecules 10 of the target substance reacting with the functional layer 130.

The piezoelectric nanobelt 126 exhibits an electrical potential difference between the first surface 122 and the second surface 124 when the electroactive cantilever 120 is deformed as a result of the target substance interacting with the functional layer 130. A first conductive member 132 is affixed to a first end 127 of the electroactive member 124 between the first end 127 and the substrate 110 and a second conductive member 134 is disposed adjacent the first end 127, opposite from the first conductive member 132.

Figure 1B:
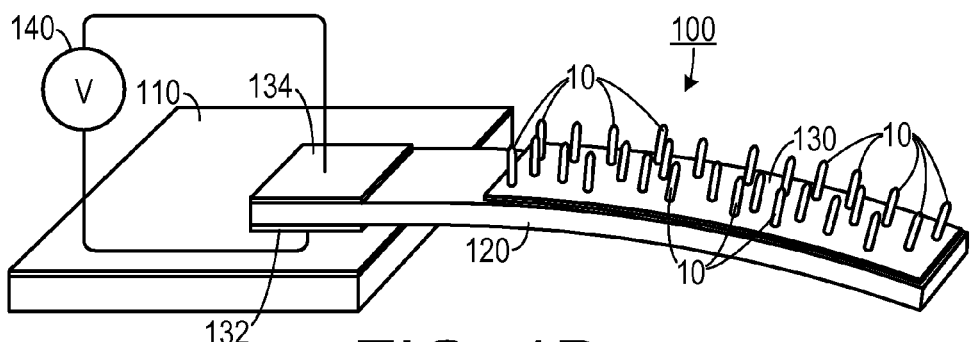

A voltage sensor 140 is configured to sense a voltage potential difference between the first conductive member 132 and the second conductive member 134. Thus, when molecules 10 of the target substance interact with the functional layer 130, as shown in FIG. 1B, the functional layer 130 expands and the piezoelectric cantilever 120 bends, thereby creating a potential difference between the first conductive member 132 and the second conductive member 134. The magnitude of this potential difference, which is sensed by the voltage sensor 140, thereby indicating the concentration of the target substance in the environment to which the sensor 100 is exposed.

Figure 2:
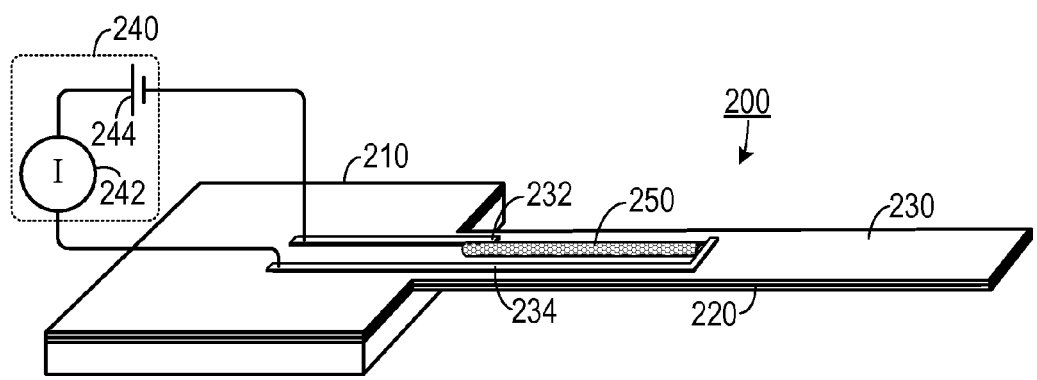
FIG. 2 is a perspective view of an embodiment including a cantilever and an electroactive member applied thereto.

As shown in FIG. 2, one embodiment employs an electroactive member 250 applied to a cantilever 220 that has been treated with a functional layer 230. In one representative example, the electroactive member 250 includes a carbon nanotube, which exhibits piezo-resistive properties. Other piezo-active materials may also be used (for example: one-dimensional nanowires that exhibit a piezo-resistive effect, nano-ribbons that exhibit a piezo-resistive effect, etc.) In this embodiment, the electrical conductivity of the electroactive member 250 changes as the cantilever 220 bends in response to reaction between the functional layer 230 and the target substance.

To measure the change in conductivity, a first contact 232 is electrically coupled to a first end of the electroactive member 250 and a second contact 234 is electrically coupled to a second end of the electroactive member 250. A conductivity sensor 240 senses the conductivity of the electroactive member 250, as measured between the first contact 232 and the second contact 234. The conductivity sensor 240 can include a voltage source 244 and a current sensor 242.

The sensors described above may be made by creating an elongated electroactive cantilever (which may be an elongated piezoelectric structure, such as a ZnO nanowire or nano-ribbon) and then functionalizing a selected surface of the elongated electroactive cantilever with a functional material that reacts with the target substance. Methods of making zinc oxide nano-ribbons are disclosed in U.S. Pat. No. 6,586,095 (see, e.g., col. 4, 1.40-col. 5, 1.6) and methods of making directional nano-ribbons are disclosed in U.S. Pat. No. 7,220,310 (see, e.g., col. 5, 1.31-col. 6, 1.19), the entirety of both of which is incorporated herein by reference. An electrical sensor is then coupled to the electroactive cantilever. The electrical contacts are then applied to the electroactive cantilever and a sensor is then coupled to the electrical contacts. The carbon nanotube embodiment may be made by manipulating a carbon nanotube onto the cantilever using an atomic force microscope.

One embodiment is a cantilever sensor that uses the piezoelectric effect of ZnO nano-ribbons (also referred to as nanobelts). By combination of e-beam lithography and sputtering (or other functionalization techniques), ZnO nano-ribbons can be coated with a functional layer on selected area. The functionalized ZnO nano-ribbon is then incorporated into a detection system with the help of a nano-manipulation tool in a focused ion beam system. The functionalized layer on the ZnO nano-ribbon will selectively bind with specific chemicals or species (i.e., the target substances) when being exposed to an environment. These binding ligands will change the surface stress due to changes in Gibbs free energy associated with adsorption processes. Consequently, the ZnO nanobelt cantilever is bended with asymmetric in surface stresses. Due to the large surface to volume ratio, this deformation can be substantial compared to the MEMS cantilevers even in a dilute bio-species environment. Also, due to the lack of central symmetry in wurtzite structures, the deflection of ZnO nanobelt (with one side fixed) causes one side surface to be stretched and the opposite side surface to be compressed. As a result of piezoelectric property, a positive potential $V^+$ ($V \propto Z_m$, $Z_m$ is the bending displacement the ZnO) and a negative potential $V^-$ are produced in the stretched and compressed side surfaces, respectively. This bias voltage due to piezoelectric effect on the deformed ZnO nanobelt provides a relatively convenient and precise way to measure the adsorbed chemical and biological species identity and qualities. By measuring the voltage drop across the two side surfaces as a result of piezoelectric discharge, the bending of the cantilever can be quantified.

In the carbon nanotube embodiment, the conductance of a carbon nanotube changes dramatically during bending due to the formation of defects and changes in band gap and conduction channels. By incorporating a carbon nanotube onto a common MEMS cantilever sensor, conductance changes of the carbon nanotube can be measured to monitor the bending of the cantilever.

This embodiment may be made by placing a carbon nanotube on a single side of coated cantilever along the longitudinal direction. The two electrical contacts may be fabricated through e-beam lithography over both ends of the carbon nanotube. When the functionalized cantilever binds with biological species on the functionalized layer, it is bended due to the surface stress change, causing bending of the carbon nanotube. Information about the absorbed species may then be acquired by measuring the conductance change due to the bending.

In one experimental embodiment, a cantilever humidity sensor was demonstrated. The device employed a single-side coated ZnO nano-ribbon functionalized with multiple layers of polymers. Upon exposure to humidity, the polymers swelled and produced an asymmetric strain across the ZnO nano-ribbon. In return, the deformation of ZnO nano-ribbon produced a piezoelectric field across the nano-ribbon, which served as the gate for controlling the flow of current along the nano-ribbon in a transistor.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. An apparatus for sensing a target substance, comprising:
   a. a substrate;
   b. an elongated electroactive cantilever comprising a piezoelectric member extending outwardly from the substrate, the piezoelectric member including a first surface and an opposite second surface; and
   c. a functional layer applied to the first surface of the piezoelectric member, the functional layer including a material that reacts with the target substance so that when the functional layer is in the presence of the target substance, the functional layer will cause a deformation in the piezoelectric member so that the piezoelectric member generates a change in an electrical property of the piezoelectric member; and
   d. an electrical sensor coupled to the electroactive cantilever and configured to sense the change in the electrical of the piezoelectric member.

2. The apparatus of claim 1, wherein the piezoelectric member comprises a piezoelectric nanobelt that is configured to exhibit an electrical potential difference between a first portion of the electroactive cantilever and a second portion of the electroactive cantilever when the piezoelectric member is deformed as a result of the target substance interacting with the functional layer.

3. The apparatus of claim 2, wherein the piezoelectric nanobelt comprises a material selected from a group consisting of: zinc oxide, wurtzite structured II-VI compounds, semiconductors and piezoelectric oxides.

4. The apparatus of claim 2, wherein the piezoelectric nanobelt includes a first end, adjacent to the substrate, and an opposite second end, the apparatus further comprising:
   a. a first conductive member disposed between the first end and the substrate; and
   b. a second conductive member disposed adjacent the first end, opposite from the first conductive member,
   wherein the electrical sensor comprises a voltage sensor configured to sense a voltage potential difference between the first conductive member and the second conductive member.

5. The apparatus of claim 1, wherein the electrical property comprises electrical conductivity.

6. The apparatus of claim 1, wherein the wherein the electroactive cantilever comprises:
   a. a flexible elongated member extending outwardly from the substrate; and
   b. a piezo-resistive member affixed to a portion of the flexible elongated member.

7. The apparatus of claim 6, wherein the piezo-resistive member comprises a structure selected from a group consisting of: carbon nanotubes, one-dimensional nanowires that exhibit a piezo-resistive effect and nano-ribbons that exhibit a piezo-resistive effect.

8. The apparatus of claim 6, wherein the electrical sensor comprises:
   a. a first contact electrically coupled to a first end of the carbon nanotube;
   b. a second contact electrically coupled to a second end of the carbon nanotube, the second end spaced apart from the first end; and
   c. a conductivity sensor that is configured to sense a conductivity of the carbon nanotube between the first contact and the second contact.

9. The apparatus of claim 8, wherein the conductivity sensor comprises:
   a. a voltage source coupled to the first contact; and
   b. a current sensor coupled to the voltage source and to the second contact.

10. A method of making a sensor for sensing a target substance, comprising the actions of:
    a. creating an elongated electroactive cantilever, the electroactive cantilever including an elongated piezoelectric member;
    b. functionalizing a selected surface of the piezoelectric member with a functional material that reacts with the target substance so that when the functional material is in the presence of the target substance, the functional material will cause a change the piezoelectric member to deform, thereby causing a change in an electrical property of the piezoelectric member; and
    c. coupling an electrical sensor to the piezoelectric member, the electrical sensor being configured to sense the change in the electrical property of the piezoelectric member.

11. The method of claim 10, wherein the action of functionalizing a selected surface of the elongated piezoelectric member comprises the action of applying a functional layer, which includes the functional material, to the piezoelectric member.

12. The method of claim 10, wherein the action of coupling an electrical sensor to the piezoelectric member comprises the actions of:
    a. applying a first electrical contact to a first side of the elongated piezoelectric member adjacent to a first end of the elongated piezoelectric member;
    b. applying a second electrical contact to a second side, opposite from the first side, of the elongated piezoelectric member adjacent to the first end of the elongated piezoelectric member;
    c. electrically coupling a voltage sensor to the first electrical contact and the second electrical contact so that the voltage sensor is configured to sense a potential difference between first electrical contact and the second electrical contact.

13. The method of claim 10, wherein the action of creating an elongated electroactive cantilever comprises the actions of:
   a. extending a flexible elongated member outwardly from a substrate; and
   b. affixing a carbon nanotube to a portion of the flexible elongated member.

14. The method of claim 13, wherein the action of coupling an electrical sensor to the electroactive cantilever comprises the actions of:
   a. electrically coupling a first contact to a first end of the carbon nanotube;
   b. electrically coupling a second contact to a second end of the carbon nanotube, the second end spaced apart from the first end; and
   c. electrically coupling a conductivity sensor to the first contact and to the second contact so that the conductivity sensor is configured to sense a conductivity of the carbon nanotube between the first contact and the second contact.

15. The method of claim 14, wherein the action of electrically coupling the conductivity sensor comprises the actions of:
   a. coupling a voltage source to the first contact; and
   b. coupling a current sensor to the voltage source and to the second contact.

16. A method of sensing a presence of a target substance in an environment, comprising the actions of:
   a. exposing to the environment an electroactive cantilever including an elongated piezoelectric member that has been functionalized with a material that causes a change in an electrical property of the elongated piezoelectric member when the material interacts with the target substance; and
   b. sensing the electrical property of the elongated piezoelectric member.

17. The method of claim 16, wherein the electrical property comprises an electrical potential difference between a first portion of the elongated piezoelectric member and a spaced apart second portion of the elongated piezoelectric member.

18. The method of claim 16, wherein the electroactive cantilever comprises an elongated member to which is affixed a carbon nanotube and wherein the electrical property comprises an electrical conductivity between a first end of the carbon nanotube and a spaced apart second end of the carbon nanotube.

* * * * *